United States Patent [19]
Blake et al.

[11] 3,995,623
[45] Dec. 7, 1976

[54] MULTIPURPOSE FLOW-DIRECTED CATHETER

[75] Inventors: Lawrence W. Blake, Costa Mesa;
Clement E. Lieber, Yorba Linda;
Harold J. C. Swan, Beverly Hills;
William Ganz, Los Angeles, all of Calif.

[73] Assignee: American Hospital Supply Corporation, Evanston, Ill.

[22] Filed: Feb. 11, 1976

[21] Appl. No.: 657,141

Related U.S. Application Data

[63] Continuation of Ser. No. 535,379, Dec. 23, 1974, abandoned.

[52] U.S. Cl. .................... 128/2.06 E; 128/2.05 D;
128/2.05 F; 128/349 R; 128/404; 128/419 P;
128/DIG. 4

[51] Int. Cl.² ........................................... A61B 5/04

[58] Field of Search ........ 128/2 M, 2.05 D, 2.05 E,
128/2.05 F, 2.05 R, 2.06 E, 2.06 R, 20 LE,
341, 349 R, 404, 418, 419 P, DIG. 4, DIG. 9

[56] References Cited

UNITED STATES PATENTS

| | | | |
|---|---|---|---|
| 2,221,138 | 11/1940 | Hendrickson | 128/349 R |
| 3,359,974 | 12/1967 | Khalil | 128/2.05 F |
| 3,448,739 | 6/1969 | Stark et al. | 128/2.05 D |
| 3,664,347 | 5/1972 | Harmjanz | 128/404 |
| 3,815,611 | 6/1974 | Denniston | 128/404 |
| 3,837,347 | 9/1974 | Tower | 128/404 |

*Primary Examiner*—William E. Kamm
*Attorney, Agent, or Firm*—Lee R. Schermerhorn

[57] ABSTRACT

The catheter is flow-directed through the heart of the patient by a balloon on its distal end to pass through the right atrium, right ventricle and into the pulmonary artery. A through lumen in the catheter tube is open at the distal end to monitor blood pressures in the pulmonary artery or a branch, or take blood samples. A thermistor proximal to the balloon permits monitoring of blood temperature in this region and thus allows the determination of cardiac output by the thermodilution technique. A second lumen has an orifice, which is characteristically located in the region of the junction of the superior vena cava and the right atrium, for pressure monitoring, infusion of liquid media, or blood sampling. A stylet in the second lumen assists in advancing the catheter and, by means of a sudden variation in stiffness, facilitates forming a sharp bend within the right ventricle to press distal electrodes against the myocardial wall which separates the left and right ventricles. Proximal electrodes on the catheter tube are positioned in the right atrium. In addition to the two lumens mentioned, a third lumen serves as a balloon inflation lumen and a fourth lumen contains the wires for the thermistor, distal electrodes and proximal electrodes.

10 Claims, 9 Drawing Figures

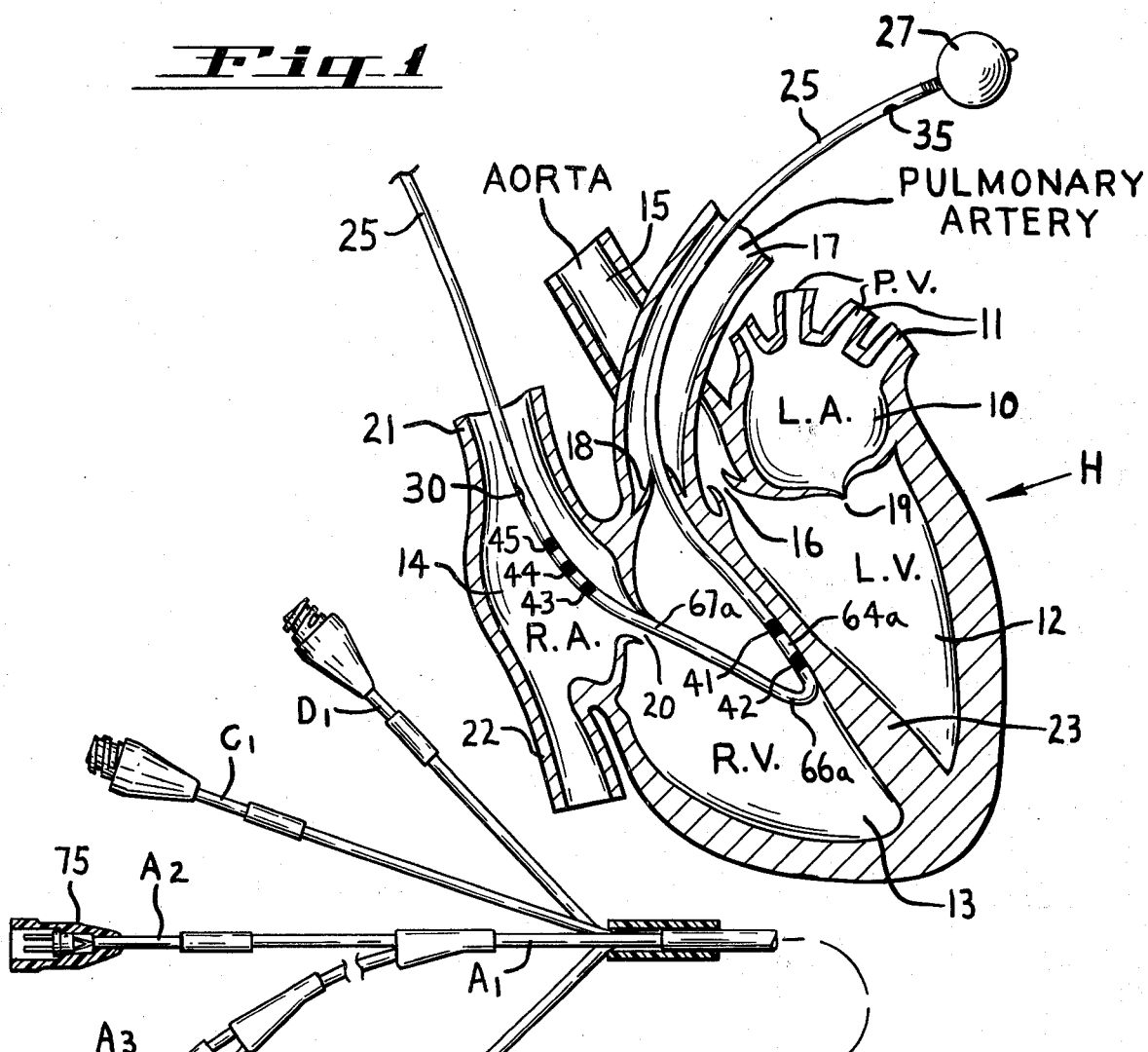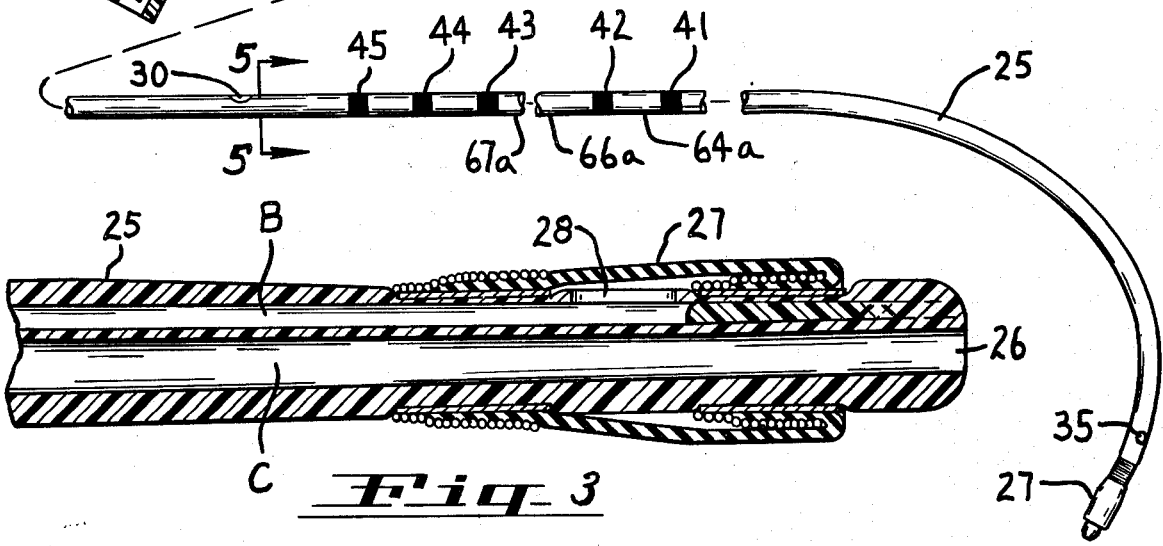

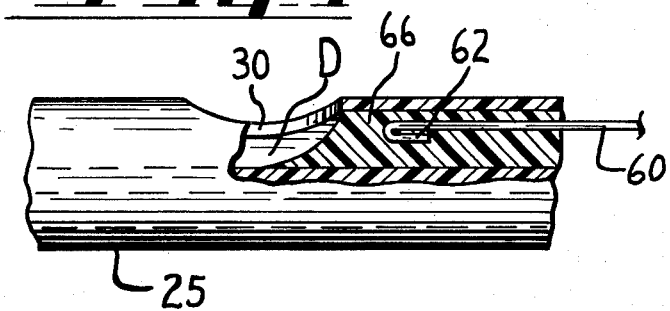
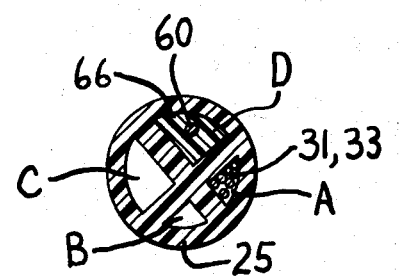
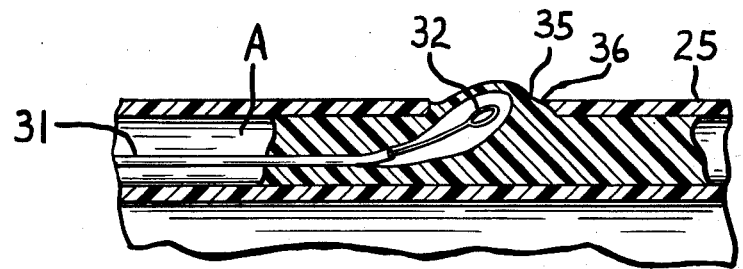
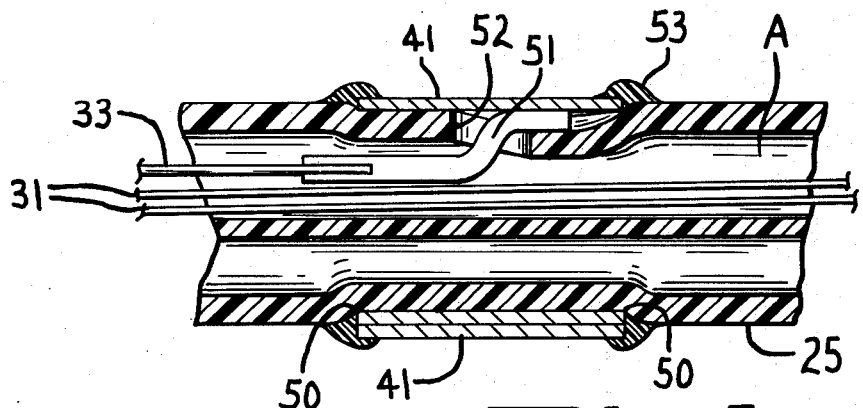
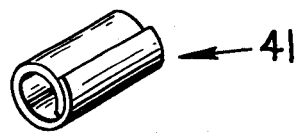
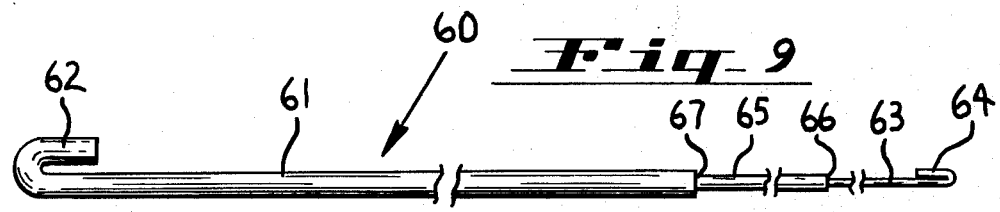

MULTIPURPOSE FLOW-DIRECTED CATHETER

CROSS REFERENCE TO RELATED APPLICATION

This application is a continuation of Ser. No. 535,379 filed Dec. 23, 1974, now abandoned.

BACKGROUND OF THE INVENTION

This invention relates to a balloon flotation electrode catheter for cardiac (EOG) monitoring and temporary transvenous pacing.

Prompt recognition and early treatment of potentially dangerous arrhythmias have significantly reduced the in-hospital mortality of patients with acute myocardial infarction and improved the management of post-surgical patients. Reliable identification and continuous accurate monitoring of cardiac rhythm in such patients is of utmost importance.

Electrocardiograms for such purposes have heretofore been recorded through the use of various types of skin electrodes. These systems suffer from several disadvantages, such as signal distortion due to patient movement, high noise to signal ratio and baseline drift. Further, because of the relatively similar amplitude and morphology of atrial and ventricular signals, the use of such systems for automated on-line arrhythmia recognition and monitoring is virtually impossible. Diagnosis and differentiation of complex arrythmias with the use of such surface electrograms is frequently difficult even for a skilled electrocardiographer because of uncertainty in the identification of the P wave.

Objects of the invention are, therefore, to provide improved equipment which will overcome the disadvantages described above, to provide improved means for direct recording of intra-atrial electrocardiograms to facilitate the diagnosis of complex cardiac arrhythmias, to provide an improved instrument for use in recording intraventricular electrograms receiving ventricualr signals of a very large magnitude, to provide means for the simultaneous recording of intraatrial and intraventricular signals, to provide means for the safe, continuous and reliable hemodynamic monitoring of cardiac function in patients with acute myocardial infarction, or following major surgery, especially where such patients present serious hemodynamic problems, and to provide a flow-directed balloon flotation electrode catheter for the purpose described, including thermodilution cardiac output determinations.

SUMMARY OF THE INVENTION

The present catheter is of the type known as a flow-directed catheter having a relatively limp shaft or tube with a balloon on its distal end. With the balloon deflated, the catheter may be inserted at the bedside into a median basilic or deep brachial vein by a cutdown or it may be inserted percutaneously from the femoral, jugular or subclavian vein. The catheter may be advanced without fluoroscopic control, electrodes on the catheter providing bipolar intracavitary electrograms which are continuously monitored along with intravascular pressures.

The balloon is inflated when the catheter has been advanced 40 cm from the tip, in a typical patient, when the right arm vein is used or at 50 cm when the left arm is used, the latter being preferred. With further advancement, the balloon on the catheter tip follows the blood flow through the right atrium and right ventricle into the pulmonary artery and then into the pulmonary capillary wedge position. When pulmonary artery or pulmonary capillary wedge pressures are recorded from the tip, the proximal and distal electrodes record characteristic intraatrial and intraventricular signals, respectively. Coiling or looping of the catheter can be recognized from simultaneous recordings of cavity electrograms and intracardiac pressures and in such event the catheter is withdrawn for a distance and then readvanced.

The catheter is finally positioned in such a way that the proximal electrodes record high right atrial electrograms, i.e., proportionately a very large atrial complex (P wave) and very small ventricular complex (QRS). At this position, characteristic intraventricular electrogram, i.e., large QRS and a very small P wave is recorded from the distal electrodes and PA pressure is recorded from the tip with the balloon deflated. When the balloon is inflated, pulmonary capillary wedge (PCW) pressure is recorded.

The invention will be better understood and additional objects and advantages will become apparent from the following description of the preferred embodiment illustrated in the accompanying drawings. Various changes may be made in the details of construction and arrangement of parts and certain features may be used without others. All such modifications within the scope of the appended claims are included in the invention.

BRIEF DESCRIPTION OF THE DRAWINGS

FIG. 1 is a diagramatic view of a heart showing the mode of operation of the catheter of the invention;

FIG. 2 is a general view of the catheter with parts broken away and parts in section;

FIG. 3 is an enlarged sectional view of the distal end of the catheter showing the balloon;

FIG. 4 is a fragmentary sectional view showing a lateral port in the catheter tube and the proximal end of the stylet;

FIG. 5 is a cross-sectional view on the line 5—5 in FIG. 2;

FIG. 6 is a fragmentary longitudinal sectional view showing the thermistor;

FIG. 7 is a fragmentary longitudinal sectional view showing one of the electrodes;

FIG. 8 is a perspective view of the electrode in FIG. 7; and

FIG. 9 is a greatly enlarged view of the stylet with parts broken away.

DESCRIPTION OF THE PREFERRED EMBODIMENT

In FIG. 1, the patient's heart has a left atrium 10 with pulmonary veins 11, left ventricle 12, right ventricle 13 and right atrium 14. Aorta 15 connects with left ventricle 12 and contains the aorta valve 16. Pulmonary artery 17 connects with right ventricle 13 and contains the pulmonary artery valve 18. Left atrium 10 communicates with left ventricle 12 through mitral valve 19. Right atrium 14 communicates with right ventricle 13 through tricuspid valve 20. Superior vena cava 21 and inferior vana cava 22 lead into right atrium 14. Myocardial wall 23 separates the left and right ventricles. Catheter 25 and the technique of passing it through the heart chambers will be described in detail.

As shown in FIG. 5 catheter tube 25 contains four lumens A, B, C and D. Lumen C is a through lumen which opens through the distal end of the catheter tube as indicated at 26 in FIG. 3. Lumen B is a balloon inflation lumen for inflating the balloon 27 through a balloon inflation opening 28. Balloon 27 is a flotation balloon preferably made according to U.S. Pat. No. 3,634,924.

The four lumens A, B, C, and D communicate with the proximal end connector tubes $A_1$, $B_1$, $C_1$, and $D_1$, respectively, in FIG. 2. Proximal connector $A_1$ communicates with three branches, $A_2$, $A_3$, and $A_4$.

A port 30 in FIGS. 1, 2, and 4 communicates with lumen D. Lumen A contains lead wires 31 for the thermistor 32 in FIG. 6 and lead wires 33 for a plurality of electrodes on the catheter tube as shown in FIG. 7. Thermistor 32 is potted in a plug of adhesive 35 at an exterior opening 36 in the lumen A. Adhesive 35 closes the lumen A at this point and indicates the position of the thermistor in FIGS. 1 and 2.

There are preferably two distal electrodes 41 and 42 and three proximal electrodes 43, 44, and 45, all identical with each other. The electrode details are shown in FIGS. 7 and 8. Each electrode, such as the electrode 41, comprises a coiled strip of spring metal with the ends slidably overlapping as shown in FIG. 8. The inside diameter of the relaxed coil is slightly smaller than the outside diameter of catheter tube 25.

In applying an electrode to the catheter tube the coil is expanded and positioned on the tube at the desired location. When the expanding force is removed the coil contracts and grips the surface of the tube. Then the tube is softened by heating, allowing the coil to contract further and indent itself into the surface of the tube as indicated at 50 in FIG. 7. This securely locks each electrode in a fixed position on the catheter tube.

The electrode is equiped with a connector 51 which extends through an opening 52 in the tube for connection with one of the lead wires 33 in lumen A. Preferably, each electrode is further sealed to the catheter tube by annular deposits of adhesive 53. The other electrodes 42–45 are mounted in the same manner and each is connected to a separate wire 33. The electrodes are used for both sensing and pacing, as will be explained. Additional electrodes may be provided for increased area contact and for His bundle sensing, if desired. Also, the catheter may be made with only one electrode, the electrode being in the position of electrode 41 or electrode 42 in the drawings, or there may be a single distal electrode and a single proximal electrode.

Catheter tube 25 contains a permanent stylet wire 60 of graduated stiffness as shown in FIG. 9. The main portion 61 of the stylet extends to a proximal end having a reverse bend 62. A distal end portion 63 of reduced diameter has a similar return bend 64 at its extremity to provide a blunt tip. An intermediate portion 65 is of intermediate thickness as shown. The stylet is made of a springy metal and the variations in thickness provide a relatively flexible distal end portion 63, a relatively stiffer proximal portion 61 and an intermediate portion 65 having an intermediate value of stiffness. A shoulder 66 marks the transition between portions 63 and 65 and a shoulder 67 marks the transition between portions 61 and 65.

The stylet 60 is permanently secured in lumen D with its proximal end 62 potted in an adhesive plug 66 as shown in FIG. 4. Adhesive 66 anchors the proximal end of the stylet and closes the lumen D on the distal side of port opening 30. The distal end of the stylet is located at the point 64a in FIGS. 1 and 2. Thus, an intermediate portion of the catheter tube between the proximal and distal electrodes is stiffened by stylet 60 and the distal end portion of the catheter extending from the distal end of the stylet at point 64a to balloon 27 is left extremely flexible and substantially limp for manipulation as a flow-directed balloon catheter.

Shoulder 66 is located at point 66a and shoulder 67 is located at point 67a in FIGS. 1 and 2. Proximal end 62 is located at point 62a. The distances of the distal and proximal electrodes from the catheter tip and the lengths of stylet portions 61, 63 and 65 vary in different catheters to accommodate heart chamber and vessel dimensions in different patients.

Thermistor lead wires 31 are connected to contact pins in an electrical connector plug 75 in FIG. 2, lead wires from the distal electrodes 41 and 42 are connected to contact pins in connector plug 76 and lead wires from proximal electrodes 43, 44, and 45 are connected to contact pins in connecter plug 77.

A particular advantage of the present catheter is that it may be inserted at the bedside without fluoroscopic control. It is inserted usually into a median basilic or deep brachial vein by a cutdown. It may however be inserted percutaneously from the femoral, jugular or subclavian vein. As the catheter is advanced, intracavitary electrograms and intravascular pressures are continuously monitored. The balloon is inflated when the catheter has been advanced 40 cm. from the tip, when the right arm vein is used, or at 50 cm. when the left arm is used. The left arm is preferable for insertion of the catheter.

With further advancement, the blood stream directs the balloon through the right atrium and right ventricle into the pulmonary artery and then into the pulmonary capillary wedge position. When pulmonary artery or pulmonary capillary wedge pressures are recorded from the tip, the proximal and distal electrodes will usually record characteristic intraatrial and intraventricular signals, respectively. Coiling or looping of the catheter can be recognized from simultaneous recordings of cavity electrograms and intracardiac pressures. For example, if proximal and distal electrodes record intraatrial and intraventricular electrograms, but a low pressure is recorded from the tip, it can be assumed that the catheter is coiled and in such case it is withdrawn and then readvanced.

The catheter is finally positioned in such a way that the proximal electrodes record high right atrial electrograms, i.e., proportionately a very large atrial complex (P wave) and a very small ventricular complex (QRS). At this position characteristic intraventricular electrogram, i.e., large QRS and very small P wave is recorded from the distal electrodes and PA pressure is recorded from the tip with the balloon deflated. When the balloon is inflated, pulmonary capillary wedge (PCW) pressure is recorded. A single distal electrode and a single proximal electrode may be used, provided that a ground electrode is located somewhere in the patients body.

In the final positioning of the catheter, shown in FIG. 1, the proximal electrodes 43, 44 and 45 and port 30 are disposed in the right atrium 14 with shoulder 67 of stylet 60 being approximately at tricuspid valve 20 as indicated at 67a. Stylet portion 65 of intermediate stiffness extends almost to the myocardial wall as indicated by the position of shoulder 66 at point 66a in FIG. 1.

This allows the stylet and catheter tube to bend abruptly, or in a desired curvature, depending upon the degree of taper in the end portion 63 of the stylet, contacting the myocardial wall, a requirement for low threshold cardiac pacing. The proximal stiffness of the stylet stabilizes the catheter within the chamber and allows this curvature to be directed into the myocardium, pressing the distal electrodes 41 and 42 firmly against the myocardial wall 23 as shown. Without this feature, the limp catheter would float freely within the chamber and contact the myocardium randomly, if at all.

Thermistor 32 at point 35 is positioned in the pulmonary artery or a branch thereof as is the distal end 26 of the through C lumen. Port 30 provides for right atrium pressure monitoring, blood sampling, or injection or infusion of liquid media for therapeutic or diagnostic purposes.

When the catheter is properly positioned as described the intraatrial and the intraventricular signals recorded with appropriate filters (atrial 50–300 and ventricular 15–300 Hz) are extremely stable. There is virtually no baseline drift and respiratory variation is small. The signal to noise ratio exceeds 50:1 in most cases. Even during movement of the patient, when the conventional surface electrogram is distorted by artifacts, both intraatrial and intraventricular electrograms remain free of artifact. The large artifact-free intraatrial and intraventicular signals with high signal to noise ratio as recorded by the present catheter makes this catheter particularly suitable for automated on-line monitoring of cardiac-rhythm.

Simultaneous recording of intra-atrial and intra-ventricular signals facilitates the diagnosis of complex arrhythmias. Certain differentiation between supraventricular tachycardia with aberrant conduction and atrio-ventricular (AV) dissociation in some patients is not possible from the analysis of the conventional surface electrograms. However, the identification of independent atrial and ventricular signals in the intracavitary electrograms as recorded by this catheter have proved beyond doubt the diagnosis of A-V dissociation.

In addition to monitoring intracardiac pressures and sensing intracardiac electrocardiograms, the present catheter also permits the emergency atrial, ventricular, or A-V sequential pacing. Contact of the ventricular electrode with the myocardial wall is absolutely necessary for consistent ventricular pacing at electrical pulse energy levels safely below the level at which ventricular fibrillation may be caused. This is not a necessity for the atrial electrodes since the atrium is a relatively smaller chamber, more sensitive to an applied electrical pulse, and not prone to the danger of fibrillation; it is not necessary to have actual contact of the electrode with the atrial wall.

The distal electrodes can provide QRS complexes of a very large magnitude and virtually free of noise, which can be used for reliable operation of any device requiring QRS triggering mechanism. Consistent counterpulsation is achieved when intraventricular QRS is used for triggering the external counterpulsation apparatus, in contrast to frequent misses observed when the conventional surface electrogram is used for triggering.

The present catheter is also adapted for hemodynamic monitoring. Pulmonary arterial pressures are recorded from the orifice terminating at the distal tip of the catheter when the balloon is deflated. Pulmonary capillary wedge pressures are recorded with the balloon inflated. Right atrial pressures can be measured through lumen D whose orifice 30 opens to the vasculature in the vicinity of the right atrium. In addition, the thermistor located on the catheter body near the distal end but proximal to the balloon, allows the determination of cardiac output by the thermodilution method.

Thus, the present catheter is of great advantage for bedside catheterization. It provides cardiac monitoring without surface leads in cardiac or post-surgical patients in whom indications for hemodynamic monitoring of ventricular function already exist and at the same time it eliminates some of the major electrical defects inherent in the use of conventional surface electrodes. Because of the increasing number of patients being simultaneously monitored in critical care areas the necessity of automated on-line computer monitoring of cardiac rhythm is becoming more and more important. Conventional surface electrograms are not suitable for such automated monitoring because of the presence of noise artifacts and baseline drift, etc., as previously mentioned.

Even when there is some catheter movement, for example during deep respiration or when the balloon is inflated to record PCW, large noise-free atrial and ventricular signals are still recorded. Noise artifacts resulting from patient movement, which are present invariably in surface electrograms, are also not seen in intracavitary electrograms obtained with the present catheter.

What is claimed is:

1. A flow-directed catheter comprising a tube having a distal artery located portion, a ventricular portion proximally of said distal portion, and an atrial portion proximal to said first two portions, an inflatable balloon on said distal portion adapted to pull the tube through the right atrium and right ventricle of the heart and into the pulmonary artery causing an entrance section of said ventricular portion of the tube to enter said ventricle in one direction and causing an exit section of said ventricular portion to exit the ventricle in a different direction, at least one ventricular electrode on said exit section of said ventricular portion adapted to be positioned in said ventricle, and means stiffening said entrance section of said ventricular portion which emerges from said atrium into said ventricle, said stiffening means producing an abrupt reduction of the stiffness of the tube on the proximal side of said electrode and forming a sharp bend between said entrance and exit sections of said ventricular portion of the tube to press said electrode against the myocardial wall between the left and right ventricles.

2. A catheter as defined in claim 1, said stiffening means comprising a stylet in said tube.

3. A catheter as defined in claim 2, said stylet having a first shoulder between a distal end portion of less thickness than an intermediate portion and a second shoulder between said intermediate portion and its proximal end portion, said proximal end portion being of greater thickness than said intermediate portion.

4. A catheter as defined in claim 1, said electrode comprising a coiled configuration of flat spring material having overlapping ends slidable on each other for ease of positioning the electrode along said tube, said coil after said positioning being indented into the surface of said tube to grip said tube and provide a substantially smooth and continuous surface on the outside of the tube.

5. A catheter as defined in claim 1 including at least one atrial electrode on said atrial portion of said tube adapted to be positioned in said right atrium.

6. A catheter as defined in claim 5, there being a plurality of said ventricle electrodes and a plurality of said atrial electrodes.

7. A catheter as defined in claim 1 including a lumen in said tube having a port opening in said atrial portion of said tube adapted to be positioned in said right atrium.

8. a catheter as defined in claim 7, said stiffening means comprising a stylet disposed in said last lumen with its proximal end secured on the distal side of said port opening.

9. A catheter as defined in claim 1, said tube having an inflation lumen for said balloon, a through lumen open at the distal end of the tube, and a lumen for an electrical conductor connected with said electrode.

10. A catheter as defined in claim 1 including a thermistor in said distal portion of said tube on the proximal side of said balloon.

* * * * *